United States Patent [19]

Fujii, deceased et al.

[11] Patent Number: 5,116,600

[45] Date of Patent: May 26, 1992

[54] COMPOSITION AND METHOD FOR INHIBITING INFLAMMATION CAUSED BY NON-PARENTERAL ADMINISTRATION OF 5-FLUOROURACIL TYPE COMPOUNDS

[75] Inventors: Setsuro Fujii, deceased, late of Kyoto, by Keiko Fujii, legal heir; Shinichiro Fujii, legal heir, Uji; Kaoruko Takada, legal heir, Ehime; Tetsuhiko Shirasaka; Masakazu Fukushima, both of Otsu, all of Japan

[73] Assignee: Otsuka Pharmaceutical Co., Ltd., Tokyo, Japan

[21] Appl. No.: 576,468

[22] PCT Filed: Jan. 4, 1990

[86] PCT No.: PCT/JP90/00015

§ 371 Date: Sep. 4, 1990

§ 102(e) Date: Sep. 4, 1990

[87] PCT Pub. No.: WO90/07334

PCT Pub. Date: Jul. 12, 1990

[51] Int. Cl.$^5$ .................. A61K 31/505; A61K 49/00
[52] U.S. Cl. ..................................... 424/10; 514/256
[58] Field of Search ........................... 514/256; 424/10

[56] References Cited

FOREIGN PATENT DOCUMENTS 55-11420  8/1980  Japan .

*Primary Examiner*—S. J. Friedman
*Attorney, Agent, or Firm*—Armstrong & Kubovcik

[57] ABSTRACT

The present invention provides a non-injection type anti-cancer composition comprising a 5-fluorouracil type compound and an oxonic acid or a pharmacologically acceptable salt thereof as effective components, the composition being capable of inhibiting inflammation development due to the 5-fluorouracil type compound, and a method of treating a cancer while inhibiting inflammation development due to the 5-fluorouracil type compound.

11 Claims, No Drawings

COMPOSITION AND METHOD FOR INHIBITING INFLAMMATION CAUSED BY NON-PARENTERAL ADMINISTRATION OF 5-FLUOROURACIL TYPE COMPOUNDS

FIELD OF THE INVENTION

The present invention relates to a non-injection type anti-cancer composition containing a 5-fluorouracil (5-FU) type compound as an anti-cancer component and capable of inhibiting inflammation from developing due to the 5-fluorouracil type compound, and to a method of treating a cancer.

PRIOR ART

5-FU type compounds have an excellent anti-tumor effect and are widely used as an anti-cancer agent for clinical purposes. However, it is known that 5-fluorouracil type compounds have the serious problems of frequently causing inflammation in oral cavity, digestive tract tissues and the like and inducing diarrhea after administration.

J. G. Niedzwicki et al. reported that the 5-FU activated by an in-vivo phosphorylating enzyme exhibits an anti-tumor activity in cancer cells but causes inflammation in normal tissues and that some kinds of pyrimidine compounds inhibit the activation of 5-FU due to the phosphorylating enzyme (Biochemical Pharmacology, Vol.33, No.15, pp.2383–2395, 1984).

Japanese Examined Patent Publication No.37766/1988 discloses that specific triazine compounds or pyrimidine compounds used conjointly with a 5-FU type compound can improve the anti-tumor effect of the 5-FU type compound without increase of its toxicity and side effect. The pyrimidine compounds tested for improved anti-tumor effects of 5-FU type compounds in the publication would be unlikely to augment the side effect of inflammation due to the 5-FU type compound but could not mitigate the side effect.

DISCLOSURE OF THE INVENTION

It is an object of the present invention to provide an excellent anti-cancer composition capable of effectively suppressing the occurrence of inflammation due to a 5-FU type compound present therein as an effective component.

It is another object of the invention to provide a method of treating a cancer while effectively suppressing the occurrence of inflammation due to a 5-FU type compound.

According to the present invention, there is provided a non-injection type anti-cancer composition comprising a 5-fluorouracil type compound and an oxonic acid or a pharmacologically acceptable salt thereof as effective components, the composition being capable of inhibiting the development of inflammation due to the 5-fluorouracil type compound.

We conducted extensive research on the improvements in the anti-cancer effects of 5-FU type compounds by numerous pyrimidine compounds known as an agent for improving the anti-tumor effect of 5-FU type compounds and on the effects of pyrimidine compounds of inhibiting the inflammation development due to the 5-FU type compound. Most of compounds heretofore proved to improve the anti-tumor effects of 5-FU type compounds had no or little inhibitory effect on inflammation. Our continued intensive investigations showed the unexpected fact that an oxonic acid can effectively suppress the occurrence of inflammation and diarrhea due to a 5-FU type compound with substantially no decrease in the anti-tumor effect of 5-FU type compound. Moreover, another discovery was that an oxonic acid can produce a high degree of the inflammation-inhibiting effect only when present in a non-injection type anti-cancer agent containing a 5-FU type compound. Thus it has been made possible according to the invention to suppress effectively inflammation as in digestive tract and oral cavity and diarrhea from occurring due to a 5-FU type compound with substantially no reduction in the anti-tumor effect of 5-FU type compound. Further the anti-cancer composition of the invention increases neither the toxicity of 5-FU type compound nor other side effects than inflammation. A further finding was that the combined use of specific 5-FU type compound and oxonic acid can inhibit inflammation development more effectively. The present invention has been accomplished based on these novel findings.

5-FU type compounds include various species heretofore known as anti-cancer agents which are all known for their tendency to induce a more or less degree of inflammation after administration. Specific examples of such 5-FU type compounds are various compounds known as the effective component of anti-cancer agents; and the 5-fluorouracil derivatives and pharmacologically acceptable salts thereof disclosed, e.g., in European Patent Publication (laid-open) No.180897, U. K. Patent Application No.2192880A, Japanese Unexamined Patent Publication No.201127/1988 and other patent publications and literature. Representative examples of 5-FU type compounds are 5-fluorouracil (5-FU), 5'-deoxy-5-fluorouridine (5'DFUR), 1-(2-tetrahydrofuranyl)-5-fluorouracil (FT-207), 3-[3-[6-benzoyloxy-3-cyano-2-pyridyloxycarbonyl)benzoyl]-1-ethoxymethyl-5-fluorouracil (Compound a); derivatives thereof and their pharmacologically acceptable salts.

An oxonic acid, specifically 1,4,5,6-tetrahydro-4,6-dioxo-1,3,5-triazine-2-carboxylic acid, has been used chiefly as a reagent for producing a hyperuricemia model [Clinical Toxicology, 13(1), 47 (1978)] but has never been used in order to suppress the occurrence of inflammation and diarrhea due to 5-FU type compounds. Oxonic acids include their keto-enol tautomers as a matter of course. Oxonic acid salts include pharmacologically acceptable acid addition salts and pharmacologically acceptable salts of basic compounds. Examples of acids capable of forming acid addition salts are hydrochloric acid, sulfuric acid, phosphoric acid, hydrobromic acid and like inorganic acids, oxalic acid, succinic acid, maleic acid, fumaric acid, malic acid, tartaric acid, citric acid, malonic acid, methanesulfonic acid, benzoic acid and like organic acids. Examples of basic compounds capable of forming pharmacologically acceptable salts of basic compounds are sodium hydroxide, potassium hydroxide, calcium hydroxide, sodium carbonate, potassium hydrogencarbonate, etc. Usable as oxonic acids are substances capable of producing oxonic acid in vivo.

According to the invention, a 5-FU type compound and an oxonic acid as the effective components are usually made into a single anti-cancer preparation. Alternatively a 5-FU type compound and an oxonic acid may be made each into respective preparations which may be taken together or separately. In other words, the oxonic acid preparation can be administered at any suitable time before or after the administration of the 5-FU type compound preparation.

As described above, the anti-cancer composition of the present invention is provided as a mixture of 5-FU type compound and oxonic acid or as two separate preparations each containing the respective components. In either case, these preparations are produced in a non-injection form by conventional methods using a suitable pharmaceutically acceptable carrier. Useful carriers include those widely used for common pharmaceuticals, such as fillers, extenders, binders, disintegrators, surfactants, lubricants and like diluents and excipients, etc.

The dosage forms of the anti-cancer composition according to the invention are not specifically limited insofar as they are not injections. The dosage form in the invention can be suitably selected according to the intended therapeutic purpose. Specific examples of the dosage form are tablets, pills, powders, solutions, suspensions, emulsions, granules, capsules, suppositories, ointments, gargles, troches, etc.

Examples of carriers useful for shaping tablets are lactose, sucrose, sodium chloride, glucose, urea, starch, calcium carbonate, kaolin, crystalline cellulose, silicic acid and like excipients, simple syrup, glucose solution, starch solution, gelatin solution, carboxymethyl cellulose, shellac, methyl cellulose, potassium phosphate, polyvinyl pyrrolidone and like binders, dried starch, sodium alginate, agar powders, laminaran powders, sodium hydrogencarbonate, calcium carbonate, polyoxyethylene sorbitan fatty acid ester, sodium lauryl sulfate, monoglyceride stearate, starch, lactose and like disintegrators, sucrose, stearin, cacao butter, hydrogenated oil and like disintegration inhibitors, quaternary ammonium base, sodium lauryl sulfate and like absorption accelerators, glycerin, starch and like moisture-retaining agents, starch, lactose, kaolin, bentonite, colloidal silicic acid and like adsorbents, purified talc, stearate, boric acid powder, polyethylene glycol and like lubricants, etc. When required, tablets may be coated with conventional materials. Examples of coated tablets are those with a sugar-, gelatin- or enteric-coating, coating film, double-layer or multi-layer.

Carriers suitable for pills are glucose, lactose, starch, cacao fats, hardened vegetable oils, kaolin, talc and like excipients, gum arabic powders, tragacanth gum powders, gelatin and like binders, laminaran, agar and like disintegrators, etc.

Carriers for suppositories include polyethylene glycol, cacao fats, higher alcohols, esters of higher alcohols, gelatin, semi-synthetic glyceride, etc.

Capsules can be made by mixing an oxonic acid, or an oxonic acid and a 5-FU type compound with a suitable carrier such as the above examples and enclosing the mixture with hard gelatin capsules, soft gelatin capsules or the like.

For paste, cream or gel, a diluent is used. Representative diluents are white petrolatum, paraffin, glycerin, cellulose derivatives, polyethylene glycol, silicone, bentonite and the like.

Carriers useful for troches include glucose, lactose, starch, cacao fats, hardened vegetable oil, kaolin, talc and the like.

Gargles can be produced by mixing oxonic acid as the effective component with a suitable carrier when so required and diluting the mixture with a diluent. Optionally gargles may be provided as a dilution type in the form of tablets, pills, powders, solutions, suspensions, emulsifiers, granules or the like which contain oxonic acid. In this case, the gargle is dissolved, suspended or emulsified in a suitable diluent immediately before use. Representative of diluents is water.

The foregoing preparations may further contain a coloring agent, preservative, perfume, flavoring, sweetener and another medication.

The amounts of 5-FU type compound and oxonic acid in the anti-cancer composition of the invention can be suitably determined without specific limitation but are usually each in the range of about 1 to about 70% by weight based on the weight of the composition.

The methods of administration in the invention are not specifically limited insofar as they are not injection methods. Non-injection methods include methods of intestinal, oral, rectal, stomatic and percutaneous administrations. The route of administration can be determined according to the dosage form, patient's age, sex and other conditions, severity of patient's symptom, etc. For example, tablets, pills, solutions, suspensions, emulsions, granules and capsules are given by oral administration, and suppositories are rectally administered. Ointments are applied to skins, intraoral mucosa or the like.

The dosage of the composition is suitably determinable in the invention according to the patient's age, sex and other conditions, degree of patient's symptom, etc. and is usually selected such that a daily dose of 5FU type compound is about 1 to about 100 mg, preferably about 4 to about 20 mg, per kilogram of the body weight and a daily dose of oxonic acid is 1 to 100 mg, preferably 2 to 30 mg, per kilogram of the body weight, While the ratio of 5-FU type compound and oxonic acid is not specifically limited, a suitable amount of oxonic acid used is about 0.05 to about 10 times, preferably about 0.2 to about 0.5 times, the weight of 5-FU type compound used. The composition of the invention may be given daily in one to four divided doses. A gargle preparation is used in the form of a solution containing about 0.1 to about 10 mg of oxonic acid per milliliter of the solution (final concentration) as in common gargles. A suitable dose of a gargle is about 100 to about 300 ml once a day. The gargle is administrable at divided doses daily.

EXAMPLES

The present invention will be described below in greater detail with reference to the following Pharmacological Test Examples and Preparation Examples.

PHARMACOLOGICAL TEST EXAMPLE 1

Test for Activity to Inhibit Inflammation Development in Digestive Tract (a) Preparation I of Test Specimens In a 1% solution of hydroxypropylmethyl cellulose was suspended 3-[3-(6-benzoyloxy-3-cyano-2-pyridyloxycarbonyl)benzoyl]-1-ethoxymethyl-5-fluorouracil (hereinafter referred to as "Compound a") to a concentration of 4.0 mg/ml. The suspension was stirred by a stirrer at room temperature for about 20 minutes and subjected to ultrasonic treatment with ice-cooling for 5 minutes, giving a test specimen (1).

Test specimens (2) to (6) were prepared in the same manner as above by adding potassium oxonate to the test specimen (1) to concentrations of 0.2, 0.5, 1.0, 2.0 and 5.0 mg/ml, respectively.

(b) Preparation II of Test Specimens

In a 1% solution of hydroxypropylmethyl cellulose was suspended each of 5'DFUR, 5-FU and UFT (5% suspension of gum arabic containing uracil and FT-207 in a ratio of 4 : 1, manufactured by Taiho Pharmaceutical Co., Ltd.) in place of Compound a used in Preparation I of Test Specimens to concentrations of 20.0, 4.0 and 4.0 mg/ml, respectively. The three suspensions were each stirred by a stirrer at room temperature for about 20 minutes and subjected to ultrasonic treatment with ice-cooling for 5 minutes, giving test specimens (7), (13) and (18), respectively.

Test specimens (8) to (12) were prepared in the same manner as above by adding potassium oxonate to the test specimen (7) to concentrations of 0.2, 0.5, 1.0, 2.0 and 5.0 mg/ml, respectively.

Test specimens (14) to (17) were prepared in the same manner as above by adding potassium oxonate to the test specimen (13) to concentrations of 0.5, 1.0, 2.0 and 5.0 mg/ml, respectively.

Similarly test specimens (19) to (22) were prepared by adding potassium oxonate to the test specimen (18) to concentrations of 0.5, 1.0, 2.0 and 5.0 mg/ml, respectively.

(c) Experiment for Anti-Cancer Activity

Yoshida sarcoma cells ($2 \times 10^4$) were subcutaneously transplanted in the back of 5 week-old male Donryu-strain rats. Twenty-four hours after the transplantation, the test specimens (1) to (22) were each orally administered to rats at a dose of 1.0 ml per 100 g of rat's body weight once a day. The test specimens were administered for 7 consecutive days. Only a 1% solution of hydroxypropylmethyl cellulose was orally administered to tumor-bearing rats as a control group.

The rats were sacrificed on the 8th day after the transplantation, and their tumors and tissues of digestive tracts were removed. The weight of the removed tumor was measured and the rate of reduction of tumor (%) was given by the following equation.

$$\text{Rate of reduction of tumor} = [1 - (T/C)] \times 100$$

T: weight of tumor (g) of rats in the group given test specimens
C: weight of tumor (g) of rats in the control group Slice samples were produced from the removed digestive tracts and observed under an optical microscope to evaluate the incidence of inflammation in digestive tracts. The incidence of inflammation was expressed in the following four grades in terms of the number of affected parts: (−) = free of inflammation; (+) = slight degree of inflammation; (++) = moderate degree of inflammation; and (+++) = high degree of inflammation. The slice samples were produced by cutting open the removed digestive tracts, washing the cut tracts with a physiological saline and immersing them in a 10% formalin solution as a neutral buffer for fixation. The incidence (%) of slight or higher degree of inflammation was indicated as the incidence of digestive tract inflammation. Table 1 below shows the results.

TABLE 1

| Test specimen | Compound a (mg/100 g) | Potassium oxonate (mg/100 g) | Number of rats (n) | Rate of tumor reduction (%) | Incidence of dig. tr. inflammation (%) | | |
|---|---|---|---|---|---|---|---|
| | | | | | Duodenum | Jejunum | Cecum |
| (1) | 4 | — | 19 | 94 | 94.7 | 73.7 | 73.7 |
| (2) | 4 | 0.2 | 6 | 95 | 91.2 | 66.7 | 33.0 |
| (3) | 4 | 0.5 | 6 | 98 | 83.1 | 66.7 | 0 |
| (4) | 4 | 0.1 | 10 | 90 | 30.0 | 20.0 | 0 |
| (5) | 4 | 2.0 | 10 | 46 | 10.0 | 0 | 0 |
| (6) | 4 | 5.0 | 5 | 24 | 0 | 0 | 0 |

| Test specimen | 5'DFUR (mg/100 g) | Potassium oxonate (mg/100 g) | Number of rats (n) | Rate of tumor reduction (%) | Incidence of dig. tr. inflammation (%) | | |
|---|---|---|---|---|---|---|---|
| | | | | | Duodenum | Jejunum | Cecum |
| (7) | 20 | — | 7 | 98 | 100 | 100 | 100 |
| (8) | 20 | 0.2 | 7 | 58 | 0 | 0 | 0 |
| (9) | 20 | 0.5 | 7 | 57 | 0 | 0 | 0 |
| (10) | 20 | 1.0 | 7 | 64 | 0 | 0 | 0 |
| (11) | 20 | 2.0 | 7 | 20 | 0 | 0 | 0 |
| (12) | 20 | 5.0 | 7 | 35 | 0 | 0 | 0 |

| Test specimen | 5-FU (mg/100 g) | Potassium oxonate (mg/100 g) | Number of rats (n) | Rate of tumor reduction (%) | Incidence of dig. tr. inflammation (%) | | |
|---|---|---|---|---|---|---|---|
| | | | | | Duodenum | Jejunum | Cecum |
| (13) | 4 | — | 7 | 87 | 100 | 100 | 57.1 |
| (14) | 4 | 0.5 | 7 | 67 | 42.8 | 28.6 | 57.1 |
| (15) | 4 | 1.0 | 7 | 53 | 57.1 | 14.3 | 0 |
| (16) | 4 | 2.0 | 7 | 58 | 42.9 | 0 | 14.3 |
| (17) | 4 | 5.0 | 7 | 46 | 14.3 | 0 | 14.3 |

| Test specimen | UFT (mg/100 g) | Potassium oxonate (mg/100 g) | Number of rats (n) | Rate of tumor reduction (%) | Incidence of dig. tr. inflammation (%) | | |
|---|---|---|---|---|---|---|---|
| | | | | | Duodenum | Jejunum | Cecum |
| (18) | 4 | — | 7 | 90 | 42.9 | 57.1 | 57.1 |
| (19) | 4 | 0.5 | 7 | 89 | 14.3 | 0 | 42.9 |
| (20) | 4 | 1.0 | 7 | 76 | 28.6 | 14.3 | 14.3 |
| (21) | 4 | 2.0 | 7 | 59 | 0 | 0 | 14.3 |
| (22) | 4 | 5.0 | 7 | 27 | 0 | 0 | 14.3 |

Note: The abbreviations "dig. tr." mean "degestive tract".

COMPARATIVE PHARMACOLOGICAL TEST EXAMPLE (a) Using Compound a (4 mg/100 g) and allopurinol known to have an activity to suppress the phosphorylation of 5-FU type compound, the relation between the rate of reduction of tumor (%) and the incidence of inflammation in digestive tracts (%) in rats was investigated in the same manner as above. Table 2 below shows the results.

TABLE 2

| Dose of allopurinol (mg/100 g) | Number of rats (n) | Rate of tumor reduction (%) | Incidence of dig. tr. inflammation (%) | | |
|---|---|---|---|---|---|
| | | | Duodeum | Jejunum | Cecum |
| — | 19 | 96 | 100 | 74 | 74 |
| 0.2 | 13 | 92 | 85 | 77 | 92 |
| 0.5 | 13 | 91 | 77 | 69 | 77 |
| 1.0 | 17 | 81 | 71 | 65 | 59 |
| 2.0 | 15 | 75 | 64 | 40 | 47 |
| 5.0 | 5 | 57 | 0 | 0 | 0 |

Note: The abbreviations "dig. tr." mean "degestive tract".

(b) Using Compound a (4 mg/100 g) and the compound disclosed in Japanese Examined Patent Publication No. 37766/1988 as capable of inhibiting the decrease of body weight due to 5-FU type compound, the relation between the rate of reduction of tumor (%) and the incidence of inflammation in digestive tracts (%) in seven rats was investigated in the same manner as above. Table 3 below shows the results.

TABLE 3

| Compound | Dose (mg/100 g) | Rate of tumor reduction (%) | Incidence of dig. tr. inflammation (%) | | |
|---|---|---|---|---|---|
| | | | Duodeum | Jejunum | Cecum |
| 5-Nitro-uracil | — | 99 | 100 | 100 | 100 |
| | 1.0 | 98 | 100 | 100 | 100 |
| | 5.0 | 91 | 100 | 100 | 100 |
| 5-Amino-uracil | — | 99 | 100 | 100 | 100 |
| | 1.0 | 98 | 100 | 100 | 100 |
| | 5.0 | 99 | 100 | 100 | 100 |
| 6-Aza-uracil | — | 99 | 100 | 100 | 100 |
| | 1.0 | 92 | 100 | 100 | 57 |
| | 5.0 | 78 | 100 | 100 | 29 |
| 6-Aza-uridine | — | 99 | 100 | 100 | 100 |
| | 1.0 | 86 | 100 | 100 | 14 |
| | 5.0 | 82 | 100 | 100 | 17 |

Note: The abbreviations "dig. tr." mean "degestive tract".

(c) Based on the results in Tables 1 to 3, a dose (A) of medicinal compounds combined with Compound a and a dose (B) thereof were determined to calculate an effect coefficient (A/B), the dose (A) being one (mg/100 g) at which the anti-tumor effect of Compound a was evidently reduced and the dose (B) being one (mg/100 g) at which the inflammation in digestive tracts was alleviated. Table 4 below shows the results.

TABLE 4

| Anti-cancer agent | Medicinal compound combined with Compound a | Dose (A) (Note 1) | Dose (B) (Note 2) | Effect coefficient (A/B) |
|---|---|---|---|---|
| Compound a | Potassium oxonate | 2 | 0.2 | 10 |
| | Allopurinol | 1 | 10 | 0.1 |
| | 6-Azauridine | 5 | >5 | <1 |
| | 6-Azauracil | 1 | >5 | <0.2 |
| 5'-DFUR | Potassium oxonate | <0.2 | <0.2 | 1 |
| 5-FU | Potassium oxonate | <0.5 | <0.5 | 1 |
| UFT | Potassium oxonate | 1 | 0.5 | 2 |

(Notes 1 and 2): The dose (A) of medicinal compounds (at which the anti-tumor effect of the anti-cancer agent was evidently reduced) is the amount in which the rate of reduction of tumor resulting from single use of anti-cancer agent was diminished by 10%. The dose (B) of medicinal compounds (at which the inflammation in digestive tracts was alleviated) is the amount in which the incidence of inflammation in digestive tracts caused by single use of anti-cancer agent was reduced by 50%.

Table 4 shows that the potassium oxonate exhibited a far higher effect coefficient against 5-FU type compound than other compounds combined with 5-FU type compound suggesting that the potassium oxonate is very useful as a compound to be combined with 5-FU type compound.

PHARMACOLOGICAL TEST EXAMPLE 2

Test for Inhibitory Effect on Diarrhea

This test was carried out in the following manner using beagles to check the effect of oxonic acid in inhibiting diarrhea development due to continued administration of a large quantity of 5-FU type compound.

Stated more specifically, four beagles each weighing 10 to 12 kg were divided into two experimental groups (A) and (B), two dogs in each group. In the experimental group (A), only Compound a was administered to a control (one dog) at a dose of 75 mg/kg/day, while Compound a and oxonic acid were administered to the test dog (one dog) at doses of 75 mg/kg/day and 20 mg/kg/day, respectively.

In the experimental group (B), Compound a alone was administered to a control (one dog) at a dose of 50 mg/kg/day, while Compound a and oxonic acid were administered to the test dog (one dog) at doses of 50 mg/kg/day and 10 mg/kg/day, respectively.

The foregoing test compounds in powder form were encapsulated with gelatin and forcibly orally administered.

After the start of oral administration, the excrement by the beagles was observed twice (morning and evening) a day. When soft feces or liquid feces were detected, the day was taken as the date of occurrence of diarrhea, and the number of days lapsed until the development of diarrhea was counted.

Table 5 below shows the results.

TABLE 5

| Group No. | Compound a (mg/kg/day) | Oxonic acid (mg/kg/day) | Number of days until diarrhea development (days) | Total dose of Compound a until diarrhea development (mg/kg) |
|---|---|---|---|---|
| (A) | | | | |
| Control | 75 | 0 | 5 | 375 |
| Test dog | 75 | 20 | 15 | 825 |
| (B) | | | | |
| Control | 50 | 0 | 7 | 350 |
| Test dog | 50 | 10 | 14 | 650 |

Table 5 shows that the control dog (to which Compound a alone was given) had diarrhea 5 to 7 days after the start of administration, whereas the test dog (to which oxonic acid was administered together with Compound a) had diarrhea later, namely 14 to 15 days after the start of administration. The conjoint use of oxonic acid allowed use of Compound a at an increased dose until the occurrence of diarrhea.

PHARMACOLOGICAL TEST EXAMPLE 3

Test for Therapeutic Effect on Intraoral Inflammation

This test was conducted in the following manner using beagles to see whether the beagle was able to recover by the application of oxonic acid from the intraoral inflammation (stomatitis) caused due to continuous administration of a large quantity of 5-FU type compound.

Two beagles of the same type as those in Pharmacological Test Example 2 were used respectively as a control (one dog) and as a test dog (one dog). Compound a (50 mg/kg) encapsulated in gelatin was forcibly orally administered to the beagles. The administration was continued for 6 consecutive days per week.

Even after the development of stomatitis, Compound a was continuously administered to the control at a dose of 50 mg/kg in the same manner as above.

An oxonic acid-containing ointment (in an amount of 1 g per application) was applied to the affected part in the oral cavity of the test dog twice (morning and evening) a day after the development of stomatitis (11th day after the start of administration of the anti-tumor agent) while Compound a was continuously administered. The ointment was prepared by adding a potassium oxonate to an olive oil-containing bleached beeswax ointment in an amount of 20 mg per gram of the ointment, and uniformly kneading the mixture.

The oral cavity of the beagles was observed with the unaided eye in administration of Compound a, and the degree of inflammation was evaluated in the following four grades in conformity with the standard for stomatitis as side effect (Japan Society for Cancer Therapy):

−... none,
+... dolor, erythema, blistering,
++... erosion, ulcer,
+++... ulcer, hemorrhage, unable to eat Table 6 below shows the results.

TABLE 6

| Group | \multicolumn{7}{c}{Number of days lapsed from start of anti-cancer agent administration} |
|---|---|---|---|---|---|---|---|
| | 5 | 10 | 15 | 20 | 25 | 30 | 35 |
| Control | − | + | +++ | +++ | (Note) | | |
| Test dog | − | + | ++ | ++ | ++ | + | ± |

(Note): The test was discontinued since the beagle was unable to eat.

Table 6 suggests that the progress of intraoral inflammation can be prevented and the dog was able to recover from the inflammation by the application of oxonic acid to the oral cavity after the development of stomatitis.

PREPARATION EXAMPLE 1

| Potassium oxonate | 60 mg |
|---|---|
| Starch | 112 mg |
| Magnesium stearate | 18 mg |
| Lactose | 45 mg |
| Total | 235 mg |

Tablets each having the foregoing composition were prepared in a conventional manner

PREPARATION EXAMPLE 2

| Compound a | 50 mg |
|---|---|
| Potassium oxonate | 25 mg |
| Starch | 112 mg |
| Magnesium stearate | 18 mg |
| Lactose | 45 mg |
| Total | 250 mg |

Tablets each having the foregoing composition were prepared in a conventional manner.

PREPARATION EXAMPLE 3

| 5′-DFUR | 250 mg |
|---|---|
| Potassium oxonate | 13 mg |
| Starch | 112 mg |
| Magnesium stearate | 20 mg |
| Lactose | 45 mg |
| Total | 440 mg |

Tablets each having the foregoing composition were prepared in a conventional manner.

PREPARATION EXAMPLE 4

| 5-FU | 50 mg |
|---|---|
| Potassium oxonate | 20 mg |
| Starch | 112 mg |
| Magnesium stearate | 18 mg |
| Lactose | 45 mg |
| Total | 245 mg |

Tablets each having the foregoing composition were prepared in a conventional manner.

PREPARATION EXAMPLE 5

| FT-207 | 200 mg |
|---|---|
| Potassium oxonate | 50 mg |
| Starch | 237 mg |
| Magnesium stearate | 18 mg |
| Lactose | 45 mg |
| Total | 550 mg |

Tablets each having the foregoing composition were prepared in a conventional manner.

PREPARATION EXAMPLE 6

| Potassium oxonate | 2 g |
|---|---|
| Glycerin | 10 g |
| Peppermint oil | 0.2 g |
| Ethanol | 10 g |
| Water | 77.8 g |
| Total | 100 g |

A gargle having the above composition per 100 ml thereof was prepared by a known method.

It is claimed:

1. An anti-cancer composition for non-parenteral administration to treat cancers susceptible to treatment with an anti-cancer compound selected from the group consisting of 5-fluorouracil, 5′-deoxy-5-fluorouridine, 1-(2-tetrahydrofuranyl)-5-fluorouracil and 3-[3-[6-benzoyloxy-3-cyano-2-pyridyloxycarbonyl)benzoyl]-1-ethoxymethyl-5-fluorouracil, comprising a) said anti-cancer compound and b) 0.05 to 10 parts by weight of oxonic acid, or a pharmacologically acceptable salt thereof, per part by weight of the anti-cancer compound.

2. An anti-cancer composition according to claim 1, wherein the anti-cancer compound is 5-fluorouracil.

3. An anti-cancer composition according to claim 1, which is in the form of a preparation for oral administration.

4. An anti-cancer composition according to claim 1, which is in the form of a suppository for rectal administration.

5. A method for inhibiting inflammation caused by the non-parenteral administration of at least one anti-cancer compound selected from the group consisting of 5-fluorouracil, 5'-deoxy-5-fluorouridine, 1-(2-tetrahydrofuranyl)-5-fluorouracil and 3-[3-[6-benzoyloxy-3-cyano-2-pyridyloxycarbonyl)benzoyl]-1-ethoxymethyl-5-fluorouracil, which comprises administering to a patient in need of inhibition of such inflammation 0.05 to 10 parts by weight of oxonic acid, or a pharmacologically acceptable salt thereof, per part by weight of the anti-cancer compound.

6. A method according to claim 5, wherein the anti-cancer compound is 5-fluorouracil.

7. A method according to claim 5, wherein the oxonic acid or pharmacologically acceptable salt thereof is administered together with the anti-cancer compound.

8. A method according to claim 5, wherein the oxonic acid or pharmacologically acceptable salt thereof is administered separately from the anti-cancer compound.

9. A method according to claim 5, wherein the anti-cancer compound is administered orally.

10. A method according to claim 5, wherein the anti-cancer compound is administered rectally.

11. A method according to any one of claims 5, 6, 7, 8, 9 or 10, wherein the amount of the anti-cancer compound administered is 1 to 100 mg per kilogram of body weight per day, and the dose of the oxonic acid or a pharmaceutically acceptable salt thereof administered to the patient is 1 to 100 mg per kilogram of body weight per day.

* * * * *

UNITED STATES PATENT AND TRADEMARK OFFICE
CERTIFICATE OF CORRECTION

PATENT NO. : 5,116,600
DATED : May 26, 1992
INVENTOR(S) : FUJII, et al

It is certified that error appears in the above-identified patent and that said Letters Patent is hereby corrected as shown below:

On the title page, please insert the following priority data information after item [87], as item [30].

--Japanese Patent Application No. 1017/1989
  Filed: January 5, 1989
  Japanese Patent Application No 122091/1989
  Filed: May 15, 1989--.

Signed and Sealed this

Twentieth Day of July, 1993

Attest:

MICHAEL K. KIRK

Attesting Officer    Acting Commissioner of Patents and Trademarks